(12) United States Patent
Black et al.

(10) Patent No.: US 7,018,979 B1
(45) Date of Patent: Mar. 28, 2006

(54) METHOD FOR USING POTASSIUM CHANNEL AGONISTS FOR DELIVERING A MEDICANT TO AN ABNORMAL BRAIN REGION AND/OR A MALIGNANT TUMOR

(75) Inventors: Keith L. Black, Los Angeles, CA (US); Nagendra S. Ningaraj, Culver City, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 0 days.

(21) Appl. No.: 09/491,500

(22) Filed: Jan. 26, 2000

(51) Int. Cl.
- *A01N 61/00* (2006.01)
- *A01N 37/18* (2006.01)
- *A61K 31/00* (2006.01)
- *A61K 38/00* (2006.01)

(52) U.S. Cl. ............................................. 514/1; 514/2
(58) Field of Classification Search .................... 514/2, 514/1
See application file for complete search history.

(56) References Cited

U.S. PATENT DOCUMENTS

| | | | |
|---|---|---|---|
| 5,112,596 A | 5/1992 | Malfroy-Camine | 424/9.1 |
| 5,124,146 A | 6/1992 | Neuwelt | 424/175.1 |
| 5,215,985 A | 6/1993 | Murphy et al. | 514/217.11 |
| 5,234,947 A | 8/1993 | Cherksey | 514/449 |
| 5,256,688 A | 10/1993 | Grover et al. | 514/422 |
| 5,262,419 A | 11/1993 | Aberg et al. | 514/275 |
| 5,268,164 A | 12/1993 | Kozarich et al. | 424/1.11 |
| 5,314,887 A | 5/1994 | Aldrich et al. | 514/252.18 |
| 5,399,587 A | 3/1995 | Garcia et al. | 514/451 |
| 5,416,097 A | 5/1995 | Erhardt et al. | 514/320 |
| 5,434,137 A | 7/1995 | Black | 514/15 |
| 5,518,499 A | 5/1996 | Agar | |
| 5,527,527 A | 6/1996 | Friden | 424/178.1 |
| 5,527,778 A | 6/1996 | Black | 514/15 |
| 5,578,599 A | 11/1996 | Diani et al. | 514/275 |
| 5,604,198 A | 2/1997 | Poduslo et al. | 514/6 |
| 5,670,477 A | 9/1997 | Poduslo et al. | 514/2 |
| 5,677,344 A | 10/1997 | Greenfield et al. | 514/592 |
| 5,679,706 A | 10/1997 | D'Alonzo et al. | 514/456 |
| 5,686,416 A | 11/1997 | Kozarich et al. | 514/15 |
| 5,695,751 A | 12/1997 | Friedman et al. | 424/94.4 |
| 5,760,230 A | 6/1998 | Schohe-Loop et al. | 544/284 |
| 5,767,160 A | 6/1998 | Kaesemeyer | |
| 5,869,509 A | 2/1999 | Romine et al. | 514/364 |
| 5,922,735 A | 7/1999 | Sit et al. | 514/312 |

FOREIGN PATENT DOCUMENTS

| | | |
|---|---|---|
| EP | 0 351 767 A2 | 1/1990 |
| EP | 0 555 681 A1 | 8/1993 |
| EP | 0 575 749 A2 | 12/1993 |
| WO | WO 91/16355 | 10/1991 |
| WO | WO 97/31654 | 9/1997 |
| WO | WO 00/23102 | 4/2000 |

OTHER PUBLICATIONS

Sabate, et al., 1996. Clinical Neuroscience, vol. 3, pp. 317-321.*

Adeagbo, A.S., *1-Ethyl-2-benzimidazolinone stimulates endothelial K(Ca) Channels and nitric oxide formation in rat mesenteric vessels*, Eur. J./ Pharmacol, 379(2-3):151-9 (Aug. 27, 1999). Abstract Only.

Akar, F., et al., *Protective effect of cromakalim and diazoxide, and proulcerogenic effect of glibenclamide on indomethacin-induced gastric injury*, Eur. J. Pharmacol, 374(3):461-70 (Jun. 25, 1999). Abstract Only.

Andrade, S.P., et al., *Pharmacological reactivity of neoplastic and non-neoplastic associated neovasculature to vasoconstrictors*, Int. J. Exp. Pathol, 79(6):425-32 (Dec. 1998). Abstract Only.

Brian, J.E., Jr., et al., *Recent insights into the regulation of cerebral circulation*, Clin. Exp. Pharmacol Physiol, 23(6-7):449-57 (Jun.-Jul. 1996). Abstract Only.

Brismar, T., et al., *Mechanism of high K+ and Tl+ uptake in cultured human glioma cells*, Cell Mol. Neurobiol, 15(3): 351-60 (Jun. 1995). Abstract Only.

(Continued)

*Primary Examiner*—Anne-Marie Falk
(74) *Attorney, Agent, or Firm*—Sherry M. Knowles, Esq.; King & Spalding LLP

(57) ABSTRACT

Disclosed are methods of selectively delivering a medicant to an abnormal brain region and/or to a malignant tumor in a mammalian subject, including a human. A medicant is administered simultaneously or substantially simultaneously with a potassium channel agonist (other than bradykinin or a bradykinin analog), such as NS-1619,1-EBIO, a guanylyl cyclase activator, a guanylyl cyclase activating protein, minoxidil, pinacidil, cromakalim, or levcromakalim, whereby the medicant is delivered selectively to the cells of the abnormal brain region and/or to the tumor, compared to normal tissues. Thus, among the disclosures is a method of treating a malignant tumor in a human subject. Also disclosed are pharmaceutical compositions that combine a potassium channel agonist together with a medicant and a kit for enhancing the delivery of a medicant to an abnormal brain region and/or to a malignant tumor.

57 Claims, 3 Drawing Sheets

OTHER PUBLICATIONS

Brismar, T., et al., *Thallium-201 uptake relates to membrane potential and potassium permeability in human glioma cells*, Brain Res., 500(1-2):30-6 (Oct. 23, 1989). Abstract Only.

Burg, M.A., et al., *NG2 proteoglycan-binding peptides target tumor neovasculature*, Cancer Res., 59(12):2869-74 (Jun. 15, 1999). Abstract Only.

Burrows, F. J., et al., *Eradication of large solid tumors in mice with an immunotoxin directed against tumor vasculature*, Proc. Natl. Acad. Science U.S.A., 90(19):8996-9000 (Oct. 1, 1993). Abstract Only.

Butt, A.M., *Effect of inflammatory agents on electrical resistance across the blood-brain barrier in pial microvessels of anaesthetized rats*, Brain Res., 696(1-2):145-50 (Oct. 23, 1995). Abstract Only.

Butt, A.M., et al., *Effect of histamine and antagonists on electrical resistance across the blood-brain barrier in rat brain-surface microvessels*, Brain Res., 569(1):100-5 (Jan. 8, 1992). Abstract Only.

Cai, S., et al., *Single-Channel characterization of the pharmacological properties of the K(Ca2+) channel of intermediate conductance in bovine aortic endothelial cells*, J. Membr. Biol., 163(2):147-58 (May 15, 1998). Abstract Only.

Chang, S.S., et al., *Five different anti-prostate-specific membrane antigen(PSMA) antibodies confirm PSMA expression in tumor-associated neovasculature*, Cancer Res., 59(13):3192-8 (Jul. 1, 1999). Abstract Only.

Chaplin, D.J., et al., *Anti-vascular approaches to solid tumour therapy: evaluation of combretastatin A4 phosphate*, Anticancer Res., 19(1A):189-95 (Jan.-Feb. 1999). Abstract Only.

Chassande, O., et al., *The Na+/K+/Cl- cotransport in C6 glioma cells, Properties and role in volume regulation*, Eur. J. Biochem., 171(3)425-33 (Feb. 1, 1988). Abstract Only.

Chess-Williams, R., et al., *In vitro investigation of the bladder-vascular selectivity of levcromakalim and YM934 in human tissues*, BJU Int., 83(9):1050-4 (Jun. 1999). Abstract Only.

Dark, G.G., et al., *Combretastatin A-4, an agent that displays potent and selective toxicity toward tumor vasculature*, Cancer Res., 57(10):1829-34 (May 15, 1997). Abstract Only.

Denekamp, J., et al., *Vasculature and microenvironmental gradients: the missing links in novel approaches to cancer therapy?* Adv. Enzyme Regul., 38:281-99 (1998). Abstract Only.

Desai, S.B., et al., *Tumor angiogenesis and endothelial cell modulatory factors*, J. Immunother., 22(3):186-211 (May 1999). Abstract Only.

D'hahan, N., et al., *A transmembrane domain of the sulfonylurea receptor mediates activation of ATP-sensitive K(+) channels by K(+) channel openers*, Mol. Pharmacol, 56(2):308-15 (Aug. 1999). Abstract Only.

Duda, T., *Mutations in the Rod Outer Segment Membrane Guanylate Cyclase in a Cone-Rod Dystrophy Cause Defects in Calcium Signaling*, Biochemistry, 38(42):13912-13919 (Oct. 19, 1999). Abstract Only.

Faraci, F.M., et al., *Responses of cerebral arterioles to N-methyl-D-aspartate and activation of ATP-sensitive potassium channels in old rats*, Brain Res., 654(2):349-51 (Aug. 22, 1994). Abstract Only.

Faraci, F.M., et al., *Potassium channels and the cerebral circulation*, Clin. Exp. Pharmacol Physiol, 23(12):1091-5 (Dec. 1996). Abstract Only.

Friebe, A., et al., *Mechanism of YC-1-induced activation of soluble guanylyl cyclase*, Mol. Pharmacol, 53(1):123-7 (Jan. 1998). Abstract Only.

Goldstein, G. W., et al., *In vitro studies of the blood-brain barrier using isolated brain capillaries and cultured endothelial cells*, Ann. N.Y. Acad. Science, 481:202-13 (1986). Abstract Only.

Harland, S. P., et al., *Expression of enthothelin(A) receptors in human gliomas and meningiomas, with high affinity for the selective antagonist PD156707*, Neurosurgery, 43(4): 890-8; discussion 898-9 (Oct. 1998). Abstract Only.

Holland, M., et al., *Effects of the BKCa channel activator, NS1619, on rat cerebral artery smooth muscle*, Br. J. Pharmacol, 117(1):119-29 (Jan. 1996). Abstract Only.

Jain, R. K., *Vascular and interstitial barriers to delivery of therapeutic agents in tumors*, Cancer Metastasis Rev., 9(3): 253-66 (Nov. 1990). Abstract Only.

Keep, R. F., et al., *Potassium transport at the blood-brain and blood-CSF barriers*, Adv. Exp. Med. Biol., 331:43-54 (1993). Abstract Only.

Konoshita, H., et al., *Differential effects of lidocaine and mexiletine on relaxations to ATP-sensitive K+ channel openers in rat aortas*, Anesthesiology, 90(4):1165-70 (Apr. 1999). Abstract Only.

Kitazono, T., et al., *Role of potassium channels in cerebral blood vessels*, Stroke, 26(9):1713-23 (Sep. 1995). Abstract Only.

Lee, Y.S., et al., *In vitro antitumor activity of cromakalim in human brain tumor cells*, Pharmacology, 49(2):69-74 (Aug. 1994). Abstract Only.

Manor, D., et al., *Interactions among calcium compartments in C6 rat glioma cells; involvement of potassium channels*, J. Physiol.(Lond.), 478(Pt.2):251-63 (Jul. 15, 1994). Abstract Only.

Miller, T.R., et al., *Pharmacological and molecular characterization of ATP-sensitive K+ channels in the TE671 huma medulloblastoma cell line*, Eur. J. Pharmacol, 37092): 179-85 (Apr. 9, 1999). Abstract Only.

Molema, G., et al., *Tumor vascular endothelium: barrier or target in tumor directed drug delivery and immunotherapy*, Pharm. Res., 14(1):2-10 (Jan. 1997). Abstract Only.

O'Donnell, M.E. et al., *Cerebral microvascular endothelial cell Na-K-CI cotransport: regulation by astrocyte-conditioned medium*, Am. J. Physiol., 268(3 Pt. 1):C747-54 (Mar. 1995). Abstract Only.

Ohizumi, I., et al., *Antibody-based therapy targeting tumor vascular endothelial cells suppresses solid tumor growth in rats*, Biochem Biophys. Res. Commun., 236(2);493-6 (Jul. 18, 1997). Abstract Only.

Ohta, Y., et al., *Tumor angiogenesis and recurrence in stage I non-small cell lung cancer*, Ann. Thorac. Surg., 68(3): 1034-8 (Sep. 1999). Abstract Only.

Panchal, R.G., *Novel therapeutic strategies to selectively kill cancer cells*, Biochem Pharmacol., 55(3):247-52 (Feb. 1, 1998). Abstract Only.

Patel, H.J., et al., *Inhibition of cholinergic neurotransmission in guinea pig trachea by NS1619, a putative activator of large-conductance, calcium-activated potassium channels*, J. Pharmacol. Exp. Ther., 286(2):952-8 (Aug. 1998). Abstract Only.

Ran, S., et al., *Infarction of solid Hodgkin's tumors in mice by antibody-directed targeting of tissue factor to tumor vasculature*, Cancer Res., 58(20):4646-53 (Oct. 15, 1998). Abstract Only.

Redrobe, J.P., et al., *The effect of the potassium channel activator, cromakalim, on antidepressant drugs in the forced swimming test in mice*, Fundam. Clin. Pharmacol., 10(6): 524-8 (1996). Abstract Only.

Rettig, W.J., et al., *Identificatgion of endosialin, a cell surface glycoprotein of vascular endothelial cells in human cancer*, Proc. Natl. Acad. Sci. U.S.A., 89(22):10832-6 (Nov. 15, 1992). Abstract Only.

Revest, P.A., et al., *The transendothelial DC potential of rat blood-brain barrier vessels in situ*, Adv. Exp. Med. Biol., 331:71-4 (1993). Abstract Only.

Revest, P.A., et al., *Transendothelial electrical potential across pial vessels in anaesthetised rats: a study of ion permeability and transport at the blood-brain barrier*, Brain Res., 652(1):76-82 (Jul. 25, 1994). Abstract Only.

Sandstrom, P.E., et al., *Identification of potassium flux pathways and their role in the cytotoxicity of estramustine in human malignant glioma, prostatic carcinoma and pulmonary carcinoma cell lines*, Eur. J. Cancer, 30A(12): 1822-6 (1994). Abstract Only.

Schilling, L., et al., *Opening of the blood-brain barrier during cortical superfusion with histamine*, Brain Res., 653(1-2):289-96 (Aug. 8, 1994). Abstract Only.

Serfass, L., et al., *Effect of heme oxygenase inhibitors on soluble guanylyl cyclase activity*, Arch. Biochem. Biophys., 359(1):8-16 (1998). Abstract Only.

Sobey, C.G., et al., *Mechanisms of bradykinin-induced cerebral vasodilatation in rats. Evidence that reactive oxygen species activate K+ channels*, Stroke, 28(11):2290-4; discussion 2295 (Nov. 1997). Abstract Only.

Smoak, I.W., *Cromakalim: embryonic effects and reduction of tolbutamide-induced dysmorphogenesis in vitro*, Teratology, 60(5):260-264 (Nov. 1999). Abstract Only.

Sugai, K. et al., *Levcromakalim decreases cytoplasmic Ca2+ and vascular tone in basilar artery of SAH model dogs*, J. Cardiovasc. Pharmacol., 33(6):868-75 (Jun. 1999). Abstract Only.

Teramoto, N. et al., *Comparative studies on the relaxing action of several adenosine 5'-triphosphate-sensitive K+ channel openers in pig urethra*, J. Smooth Muscle Res., 35(1):11-22 (Feb. 1999). Abstract Only.

Thorpe, P. E. et al., *Antibody-directed targeting of the vasculatlure of solid tumors*, Breast Cancer Res. Treat., 36(2):237-51 (1995). Abstract Only.

Toyoda, K. et al., *Role of ATP-sensitive potassium channels in brain stem circulation during hypotension*, Am. J. Physiol., 273(Pt. 2):H1342-6 (Sep. 1997). Abstract Only.

Van Hinsbergh, V. W. et al., *Angiogenesis and anti-angiogenesis: perspectives for the treatment of solid tumors*, Ann. Oncol., 10 Supl 4:60-3 (1999). Abstract only.

Walter, J. J. et al., *Angiostatin binds to smooth muscle cells in the coronary artery and inhibits smooth muscle cell proliferation and migration in vitro*, Arterioscler. Throm. Vasc. Bio., 19(9):2041-8 (Sep. 1999). Abstract Only.

Wickenden, A.D. et al., *Comparison of the effects of the K(+)-channel openers cromakalim and minoxidil suplhate on vascular smooth muscle*, Br. J. Pharmacol., 103(1):1148-52 (May 1991). Abstract Only.

XP-002195899—Oak, Z. et al., *Effects of Cyclic GMP on Microvascular Permeability of the Cerebral Cortex*, Microvascular Research, vol. 58, pp. 35-40 (1999).

XP-002195900—*Role of nitric oxide in histamine-induced increases in permeability of the blood-brain barrier*, Mayhan, William G., Brain Research, vol. 743, pp. 70-76 (1996).

XP-002195901—Bartus, R. T. et al., *Controlled Modulation of BBB Permeability Using the Bradykinin Agonist, RMP-07*, Experimental Neurology, vol. 142, pp. 14-28 (1996).

International Search Report re PCT/US01/02743, P mailed Apr. 26, 2002.

Armstead, W.M., *Contribution of kca channel activation to hypoxic cerebrovasodilation does not involve NO*, Brain Res., 799:44-48 (1998). Abstract Only.

Barna, M., et al., *Activation of type III nitric oxide synthase in astrocytes following a neurotropic viral infection*, Virology, 223: 331-343 (1996).

Becker, E.M., et al., *The vasodilator-stimulated phosphoprotein(VASP): target of YC-1 and nitric oxide effects in human and rate platelets*. J Cardiovasc Pharmacol. 35(3):390-7 (2000). Abstract Only.

Boje, K. M., *Inhibition of nitric oxide synthase attenuates blood-brain barrier disruption during experimental meningitis*, Brain Research, 720:75-83 (1996).

Brandt, L., et al., *Effects of topical application of calcium antagonist (nifedipine) on feline cortical pial microvasculature under normal conditions and in focal ischemia*, Journal of Cerebral Blood Flow and Metabolism, 3:44-50 (1983).

Brioni, J.D., et al., *Activators of soluble guanylate cyclase for treatment of male erectile dysfunction*, International Journal of Impotence Research, 14:8-14 (2002).

Bychkov, R., et al. *Calicum-activated potassium channels and nitrate-induced vasodilation in human coronary arteries*, J. Pharacol Exp Therap, 285:293-8 (1998). Abstract Only.

Chandran, S., et al., *Nitric oxide: concepts, current perspectives and future therapeutic implications*, Indian Journal of Pharmacology, 30:351-366 (1998).

Chi, O.Z., et al. *Effect of inhibition of nitric oxide synthase on blood-brain barrier transport in focal cerebral ischemia*, Pharmacologylogy, 48:367-373 (1994).

Cloughesy, T.F., et al., *Pharmacological blood-brain barrier modification for selective drug delivery*, Journal of Neuro-Oncology, 26:125-132 (1995).

Feelisch, M., *The use of nitric oxide donors in pharmacological studies*, Naunyn-Schmiedeberg's Arch Pharmcol, 358:113-122 (1998).

Fukao, M., et al., *Cyclic GMP-dependent protein kindase activates cloned BKCa channels expressed in mammalian cells by direct phophorylation at serine 1072*, J Biol Chem, 274(16):10927-35 (1999).

Fukumura, D., et al., *Role of nitric oxide in angiogenesis and microcirculation in tumors*, Cancer and Metastasis Reviews, 17:77-89 (1998).

He, P., et al., *cGMP modulates basal and activated microvessel permeability independenty of [Ca2+]i*, Am J Physiol, 274:H1865-74 (1998). Abstracts Only.

Herrera, G.M., et al., *Maintained vasodilatory response to cromakalim after inhibition of nitric oxide synthesis*, J Cardiovasc Pharmacol, 31:921-9 (1998). Abstract Only.

Holschermann, H., et al., *Dual role of cGMP in modulation of macromolecule permeability of aortic endothelial cells*, Am J Physiol, 272:H91-8 (1997). Abstract Only.

Hongli, X., et al., *Opening blood-brain-barrier by intracarotid infusion of papaverine in treatment of malignant cerebral glioma*, Chinese Medical Journal, 111 (8):751-753 (1998).

Hurst, R.D., et al., *Nitric oxide-induced perturbations in a cell culture model of the blood-brain barrier*, Journal of Cellular Physiology, 167:89-94 (1996).

Inamura, T., et al., *Intracarotid histamine infusion increases blood tumour permeability in RG2 glioma*, Neurological Research, 16:125-128 (1994).

Inamura, T., et al., *Intracarotid infusion of RMP-7, a bradykinin analog: a method for selective drug delivery to brain tumors*, J Neurosurg, 81:752-758 (1994).

Janigro, D., et al., *Regulation of blood-brain barrier endothelial cells by nitric oxide*, Circulation Research, 75:528-528 (1994).

Kimura, M., et al., *Responses of human basilar and other isolated arteries to novel nitric oxide donors*, J Cardiovasc Pharmacol, 32: 695-701 (1998). Abstract Only.

Koesling, D., *Modulators of soluble guanylyl cyclase*, Naunyn-Schmiedeberg's Arch Pharmacol, 358:123-126 (1998).

Liu, Y., et al., *Repeated, short-term ischemia augments bradykinin-mediated opening of the blood-tumor barrier in rats with RG2 glioma*, Neurological Research, 23:631-639 (2001).

Lohse, M.J., et al., *Pharmacology of NO:cGMP signal transduction*, Naunyn-Schmiedeberg's Arch Pharmcol, 358: 111-112 (1998).

Matukado, T., et al., *Selective Increase in Blood Tumor Permeability by Calcium Antagonists in Transplanted Brain Tumors*, Acta Neurochir, 60:403-405 (1994).

Mayer, B., et al., *Nitric oxide synthases: catalytic function and progress toward selective inhibitions*, Naunyn-Schmiedeberg's Arch Pharmcol, 358:127-133 (1998).

Mayham, W.G., *Role of nitric oxide in histamine-induced increases in permeability of the blood-brain barrier*, Brain Research, 743:70-76 (1996).

Mayhan, W.G., et al., *Glutamate-induced disruption of the blood-brain barrier in rats*, Stroke, 27:965-970 (1996).

Nakano, S., et al., *Increased brain microvessel permeability after intracarotid bradykinin infusion is mediated by nitric oxide*, Cancer Research, 56;4027-4031 (1996).

Ningaraj, N.S., et al., *Role of ATP-sensitive K+ channels in blood-brain tumor barrier permeability*, Congress of Neurological Surgeons Annual Meeting, 50th Anniversary Celebration, Sep. 23-28, 2000, Henry B. Gonzalez Convention Center, San Antonio, Texas, ABSTRACT No. 4309, p. 215.

Ningaraj, N.S., et al., *Ca2+ -dependent K+ channels are a key regulatory of blood-brain tumor barrier permeability*, Congress of Neurological Surgeons Annual Meeting, 50th Anniversary Celebration, Sep. 23-28, 2000, Henry B. Gonzalez Convention Center, San Antonio, Texas, ABSTRACT No. 428, p. 219.

Ningaraj, N.S., et al., *Nitric oxide donors increase blood-brain tumor barrier permeability via Kca channels*, Society for Neuroscience, 30th Annual Meeting, New Orleans, LA, Nov. 4-9, 2000, 26 Part 1, p. 338, ABSTRACT No. 126.8.

Ningaraj, N.S., et al., *Regulation of blood-brain tumor barrier permeability by calcium-activated potassium channels*, The Journal of Pharmacolgy, Jun. 2002, 301:838-851.

Pardrige, W., et al., *Blood -brain barrier and new approaches to drug delivery*, West J Med, 156:281-286 (1992).

Robertson, B.E., et al., *cGMP-dependent protein kinase activates Ca-activated K channels in cerebral artery smooth muscle cells*, Am J Physiol, 265:C299-C303 (1993).

Sobey, C.G., et al., *Inhibitory effect of 4-aminopyridine on responses of the basilar artery to nitric oxide*, Br J Pharmacol, 126:1437-43 (1999). Abstract Only.

Salom, J.B., et al., *Relaxant effects of sodium nitroprusside and NONOates in rabbit basilar artery*, Pharmacology, 57:79-97 (1998). Abstract Only.

Salom, J.B., et al., *Comparative relaxant effects of the NO donors sodium nitroprusside, DEA/NO and SPER/NO in rabbit carotid arteries*, Gen Pharmacol, 32:75-59 (1999). Abstract Only.

Salom, J.B., et al., *Relexant effects of sodium nitroprusside and NONates in goat middle cerebral artery: delayed impairment of global ischemia-reperfusion*, Nitric Oxide, 3:85-93 (199). Abstract Only.

Shukla, A., et al., *Nitric oxide-dependent blood-brain barrier permeability alteration in the rat brain*, Experientia, 52:136-140 (1996).

Smolenski, A., et al., *Functional analysis of cGMP-dependent protein kinases I and II as mediators of NO/cGMP effects*, Naunyn-Schmiedeberg's Arch Pharmacol, 358:134-138.

Sugita, M., et al., *Cyclic GMP-specific phosphodieterase inhibition and intracarotid bradykinin infusion enhances permeability in brain tumors*, Cancer Research, 58:914-920 (1998).

Takayasu, M., et al., *Effects of calcium antagonists on intracerebral penetrating arteriolesi in rats*, J Neurosurg, 69:104-109 (1988).

Uchida, M., et al., Overexpression of bradykinin type 2 receptors on glioma cells enhances bradykinin-mediated blood-brain tumor varrier permeability increase, Neurological Research, 24:739-745.

Uchida, M., et al., *Cyclic GMP-dependent blood-brain tumor barrier permeability is not mediated by cyclic GMP-dependent protein kinase*, Congress of Neurological Surgeons Annual Meeting, 50th Anniversary Celebration, Sep. 23-28, 2000, Henry B. Gonzalez Convention center, San Antonio, Texas, ABSTRACT No. 440, p. 220.

Vodovotz, Y., et al., *Regulation of transforming growth factor beta 1 by nitric oxide*, Cancer Res, 59:2142-9 (1999). Abstract Only.

Yukabu, M.A., *Hematoma-induced enhanced cerebral vasoconstriction to leukotriene C4 and endothelin-1 piglets: role of prostanoids*, Pediatr Res, 38:119-23 (1995). Abstract Only.

Tocris Web Page, http://www.tocris.com/cat/nodonorstxt.html No Donors/ Precursors, pp. 1-2, Downloaded May 31, 2000.

Sigma-Aldrich Web page, http://vsearch.sial.com/search 97cgi/s97-cgi, downloaded May 31, 2000.

* cited by examiner

METHOD FOR USING POTASSIUM CHANNEL AGONISTS FOR DELIVERING A MEDICANT TO AN ABNORMAL BRAIN REGION AND/OR A MALIGNANT TUMOR

BACKGROUND OF THE INVENTION

Throughout the application various publications are referenced in parentheses. The disclosures of these publications in their entireties are hereby incorporated by reference in the application in order to more fully describe the state of the art to which this invention pertains.

1. The Field of the Invention

This invention relates to the medical arts. In particular, it relates to a method of enhancing the delivery of a medicant across abnormal microvasculature to a tissue requiring treatment.

2. Discussion of the Related Art

Pathologic neovascularization, i.e., the proliferation or development of new blood vessels, is essential for the growth and spread of primary, secondary and metastatic malignant tumors. It is known that certain properties of the new capillaries and arterioles constituting the neomicrovasculature in solid tumors differ from those of normal microvasculature. (J. Denekamp et al., *Vasculature and microenvironmental gradients: the missing links in novel approaches to cancer therapy?*, Adv. Enzyme Regul. 38:281–99 [1998]). Neomicrovasculature induced by angiogenic factors from malignant cells was reported to possess altered pharmacological reactivity to some vasoconstricting agents, compared with neomicrovasculature that was not induced by neoplastic cells. (S. P. Andrade and W. T. Beraldo, *Pharmacological reactivity of neoplastic and non-neoplastic associated neovasculature to vasoconstrictors*, Int. J. Exp. Pathol. 79(6):425–32 [1998]).

A number of proposed cancer treatments have been based on differences between neomicrovasculature and normal microvasculature. For example, combretastatin A-4 was shown to cause vascular damage and occlusion selectively in the blood vessels of malignant tumors compared to normal blood vessels. (G. G. Dark et al., *Combretastatin A-4, an agent that displays potent and selective toxicity toward tumor vasculature*, Cancer Res. 57(10): 1829–34 [1997]; D. J. Chaplin et al., *Anti-vascular approaches to solid tumour therapy: evaluation of combretastatin A4 phosphate*, Anti-cancer Res. 19(1A):189–95 [1999]). Monoclonal antibodies have been directed to antigens and antigenic combinations specific to endothelial cells of pathologic neovasculature, such as vascular cell adhesion molecule (VCAM)-1, phosphatidylserine (PS), the glycoprotein endosialin, and prostate-specific membrane antigen (PSMA), with the aim of selectively inducing thrombosis in neovasculature. (E.g., S. Ran et al., *Infarction of solid Hodgkin's tumors in mice by antibody-directed targeting of tissue factor to tumor vasculature*, Cancer Res. 58(20):4646–53 [1998]; I. Ohizumi et al., *Antibody-based therapy targeting tumor vascular endothelial cells suppresses solid tumor growth in rats*, Biochem. Biophys. Res. Commun. 236(2):493–96 [1997]; S. S. Chang et al., *Five different antiprostate-specific membrane antigen (PSMA) antibodies confirm PSMA expression in tumor-associated neovasculature*, Cancer Res. 59(13):3192–98 [1999]; W. J. Rettig et al., *Identification of endosialin, a cell surface glycoprotein of vascular endothelial cells in human cancer*, Proc. Natl. Acad. Sci. USA 89(22):10832–36 [1992]). But taken alone, shutting down blood flow through the neomicrovasculature to malignant tumors may not necessarily result in stopping tumor growth, because actively proliferating populations of neoplastic cells at the periphery of solid tumors may have access to blood supplied by normal microvasculature. (E.g., D. J. Chaplin et al. [1999]).

Consequently, other conventional and novel therapeutic modalities will continue to be of value in the treatment of malignant, solid tumors. However, the efficacy of novel therapeutic agents, including cytotoxic chemotherapeutic agents, monoclonal antibodies, cytokines, effector cells, and viral particles has been limited by their ability to reach their targets in vivo in adequate quantities. (E.g., R. K. Jain, *Vascular and interstitial barriers to delivery of therapeutic agents in tumors*, Cancer Metastasis Rev. 9(3):253–66 [1990]). An important limiting factor is the low permeability to macromolecules and viral particles of neomicrovasculature supplying the tumors.

This problem of microvascular permeability is especially acute with respect to malignant tumors of the central nervous system. These malignancies are usually fatal, despite recent advances in the areas of neurosurgical techniques, chemotherapy and radiotherapy. In particular, there are no standard therapeutic modalities that can substantially alter the prognosis for patients with malignant tumors of the brain, cranium, and spinal cord. For example, high mortality rates persist for patients diagnosed with malignant medulloblastomas, malignant meningiomas, malignant neurofibrosarcomas and malignant gliomas, which are characterized by infiltrative tumor cells throughout the brain. Although intracranial tumor masses can be debulked surgically, treated with palliative radiation therapy and chemotherapy, the survival associated with intracranial tumors, for example, a glioblastoma, is typically measured in months. The development of new therapeutic modalities against solid brain tumors largely depends on transvascular delivery of the potential therapeutic agent.

Transvascular delivery of chemotherapeutic agents and viral particles to tumor cells or other abnormal brain tissue is hampered by the blood-brain barrier, particularly the blood-tumor barrier found in brain tumors. The blood-brain barrier is a transvascular permeability barrier thought to result from the interendothelial tight junctions formed by the cerebrovascular endothelial cells of brain capillaries and arterioles in both normal and abnormal brain tissue. The blood-brain barrier protects the brain from changes in the composition of the systemic blood supply (e.g., in electrolytes) or from blood-borne macromolecules, such as immunoglobulins or other polypeptides, and prevents the transvascular delivery of many exogenously supplied pharmaceutical agents to brain tissues.

The treatment of brain tissue abnormalities, such as tumors, often involves the use of pharmaceutical agents with a significant toxicity of their own, making it highly desirable to be able to preferentially direct such agents to the abnormal or malignant tissue. While, there has been a great deal of interest in developing techniques which are capable of opening the blood-brain barrier to allow transport of pharmaceutical agents to the brain. Few of these methods are capable of selectively opening the blood-brain barrier only in the abnormal brain tissue while leaving the blood-brain barrier in the normal brain tissue intact.

For example, Neuwelt et al. used an intracarotid injection of hypertonic mannitol to osmotically disrupt the blood-brain barrier. They reported that this enhanced the uptake by brain tissue of inactivated HSV-1 particles that were administered immediately afterward by intracarotid bolus injection. (E. A. Neuwelt et al., *Delivery of ultraviolet-inactivated 35S- herpesvirus across an osmotically modified blood-brain barrier*, J. Neurosurg. 74(3):475–79 [1991];

Also, S. E. Doran et al., *Gene expression from recombinant viral vectors in the central nervous system after blood-brain barrier disruption*, Neurosurgery 36(5):965–70 [1995]; G. Nilaver et al., *Delivery of herpesvirus and adenovirus to nude rat intracerebral tumors after osmotic blood-brain barrier disruption*, Proc. Natl. Acad. Sci. USA 92(21): 9829–33 [1995]).

Intracarotid infusion of leukotriene $C_4$ ($LTC_4$) selectively increases the permeability in brain tumor capillaries without affecting the permeability in normal brain capillaries. The effect of $LTC_4$ on brain tumor capillaries is, however, limited to small molecules and it can only slightly increase the permeability of those small molecules in abnormal brain tissue relative to normal. Accordingly, $LTC_4$ does not significantly increase the delivery of some larger water soluble molecules to brain tumors or other abnormalities.

The vasoactive nonopeptide bradykinin and agonists or polypeptide analogs thereof (e.g., receptor-mediated permeabilizers [RMPs]) have been injected intravenously to increase blood-brain barrier permeability to co-administered neuropharmaceutical or diagnostic agents. (B. Malfroy-Camine, Method for increasing blood-brain barrier permeability by administering a bradykinin agonist of blood-brain barrier permeability, U.S. Pat. No. 5,112,596; J. W. Kozarich et al., Increasing blood brain barrier permeability with permeabilizer peptides, U.S. Pat. No. 5,268,164). Intracarotid infusion of bradykinin will selectively increase permeability 2- to 12-fold in brain tumor and ischemic brain capillaries for molecules ranging in molecular weight from 100 to 70,000 Daltons (Inamura, T. et al., *Bradykinin selectively opens blood-tumor barrier in experimental brain tumors*, J. Cereb Blood Flow Metab. 14(5):862–70 [1994]). Bradykinin does not increase permeability in the normal blood brain barrier except at very high doses. (Wirth, K. et al., *DesArg9-D-Arg[Hyp3,Thi5,D-Tic7,Oic8]bradykinin (desArg10-[Hoe140]) is a potent bradykinin B1 receptor antagonist*, Eur. J. Pharmacol. 205(2):217–18 [1991]). Opening of the blood-tumor barrier by bradykinin is transient, lasting 15 to 20 minutes. (Inamura et al. [1994]). After opening of abnormal brain capillaries with bradykinin, the capillaries become refractory to the bradykinin effect for up to 60 minutes. (Inamura et al [1994]).

A method for selectively delivering to abnormal brain tissue a neuropharmaceutical agent (e.g., 5-fluorouracil, cisplatin, methotrexate, or monoclonal antibodies) or a diagnostic agent (e.g., technicium-99 glucoheptonate, gallium-EDTA, and ferrous magnetic or iodinated contrasting agents) employed intracarotid infusion of bradykinin, or a bradykinin analog, such as RMP-7; the bradykinin or bradykinin analog was administered approximately contemporaneously with the agent. (K. L. Black, Method for selective opening of abnormal brain tissue capillaries, U.S. Pat. Nos. 5,527,778 and 5,434,137). Enhanced transvascular delivery of HSV-derived viral particles to malignant cells in the brains of rats was also achieved by disrupting the blood-brain barrier with bradykinin or RMP-7. (N. G. Rainov, *Selective uptake of viral and monocrystalline particles delivered intra-arterially to experimental brain neoplasms*, Hum. Gene. Ther. 6(12):1543–52 [1995]; N. G. Rainov et al., *Long-term survival in a rodent brain tumor model by bradykinin-enhanced intra-arterial delivery of a therapeutic herpes simplex virus vector*, Cancer Gene Ther. 5(3):158–62 [1998]; F. H. Barnett et al., *Selective delivery of herpes virus vectors to experimental brain tumors using RMP-7*, Cancer Gene Ther. 6(1):14–20 [1999]).

The calcium-activated potassium channel ($K_{Ca}$) is an important regulator of cerebral blood vessel tone (Nelson M T, Quayle J M. *Physiological roles and properties of potassium channels in arterial smooth muscle*, Am. J. Physiol. 268(4 Pt 1): C799–822[1995]). The $K_{Ca}$ channel is ubiquitously distributed in tissues as $\alpha$ and $\beta$ subunits. Its activity is triggered by depolarization and enhanced by an increase in cytosolic calcium di-cation ($Ca^{2+}$). A local increase in $Ca^{2+}$ is sensed by the extremely sensitive brain $\alpha$-subunit of the $K_{Ca}$, directed towards the cytoplasm in the cell, that allows a significant potassium cation flux through these channels.

Under conditions when intracellular cyclic 3', 5' adenosine monophosphate (cAMP) concentration rises in vascular endothelium (e.g. hypoxia), ATP-sensitive potassium channels ($K_{ATP}$) may also play a role. (J. E. Brian et al., *Recent insights into the regulation of cerebral circulation*, Clin. Exp. Pharmacol. Physiol. 23(6–7):449–57 [1996]). Minoxidil sulfate and chromakalim are reported to be activators of $K_{ATP}$. (A. D. Wickenden et al., *Comparison of the effects of the K(+)-channel openers cromakalim and minoxidil sulphate on vascular smooth muscle*, Br. J. Pharmacol, 103(1): 1148–52 [1991]).

Treatments directed to the use of potassium channel activators or agonists have been taught for disorders including hypertension, cardiac and cerebral ischemia, nicotine addiction, bronchial constriction, and neurodegenerative diseases, but not particularly for the treatment of malignant tumors. (Erhardt et al., Potassium channel activators/openers, U.S. Pat. No. 5,416,097; Schohe-Loop et al., 4,4'-bridged bis-2,4-diaminoquinazolines, U.S. Pat. No. 5,760, 230; Sit et al., 4-aryl-3-hydroxyquinolin-2-one derivatives as ion channel modulators, U.S. Pat. No. 5,922,735; Garcia et al., Biologically active compounds, U.S. Pat. No. 5,399, 587; Cherksey, Potassium channel activating compounds and methods of use thereof, U.S. Pat. No. 5,234,947).

Bradykinin is thought to increase $[Ca^{2+}]_i$ and thus may activate $K_{Ca}$ channels. While some other known activators of $K_{Ca}$ do not act as vasodilators, for example, 1,3-dihydro-1-[2-hydroxy-5-(trifluoromethyl)phenyl]-5-(trifluoromethyl)-2H-benzimidazol-2-one (NS-1619; M. Holland et al., *Effects of the BKCa channel activator, NS1619, on rat cerebral artery smooth muscle*, Br J Pharmacol, 117(1): 119–29 [1996]), evidence is accumulating that $K_{Ca}$ may play an important role in vasodilatation mediated by vasodilators, such as bradykinin, NO-donors, cGMP, and guanylate cyclase activators. (Berg T., Koteng O., *Signaling pathways in bradykinin-and nitric oxide-induced hypotension in the normotensive rat; role of K+-channels*, Br. J. Pharmacol.; 121(6):1113–20 [1997]; Bolotina, V. M. et al., *Nitric oxide directly activates calcium-dependent potassium channels in vascular smooth muscle*, Nature 368(6474):850–3 [1994]; Robertson, B. E., et al., *cGMP-dependent protein kinase activates Ca-activated K channels in cerebral artery smooth muscle cells*, Am. J. Physiol. 265(1 Pt 1):C299–303 [1993]; Sobey, C. G. et al., *Mechanisms of bradykinin-induced cerebral vasodilatation in rats. Evidence that reactive oxygen species activate K+ channels*, Stroke 28(11):2290–4; discussion 2295 [1997]; C. G. Sobey and F. M. Faraci, *Effect of nitric oxide and potassium channel agonists and inhibitors on basilar artery diameter*, Am. J. Physiol. 272(1 Pt 2):H256–62 [1997]).

Bradykinin's action as a powerful vasodilator is disadvantageous when using bradykinin to open the blood-brain barrier to therapeutic anticancer agents. Bradykinin or its analogs may adversely lower blood pressure, reduce cerebral blood flow, or contribute to brain edema in some patients. (E.g., A. M. Butt, *Effect of inflammatory agents on electrical resistance across the blood-brain barrier in pial*

*microvessels of anesthetized rats*, Brain Res. 696(1–2): 145–50 [1995]). In addition, bradykinin constricts smooth muscle and stimulates pain receptors.

Consequently, there is still a definite need to maximize the effectiveness of a wide variety of therapeutic agents through enhanced selective transvascular delivery to malignant tumors, including those of the central nervous system, and/or to other abnormal brain regions. These and other benefits the present invention, employing potassium channel agonists, provides as described herein.

SUMMARY OF THE INVENTION

The present invention relates to a method of delivering a medicant to an abnormal brain region in a mammalian subject, including a human. The method includes administering to the subject a potassium channel agonist other than bradykinin or a bradykinin analog, for example NS-1619 or minoxidil, under conditions and in an amount sufficient to increase the permeability to the medicant of a capillary or arteriole delivering blood to cells of the abnormal brain region in the subject. Simultaneously or substantially simultaneously with the potassium channel agonist, the medicant is administered, so that the medicant is delivered selectively to the cells of the abnormal region compared to normal brain regions, due to the increased permeability of capillaries and arterioles supplying the abnormal brain region. The method is particularly valuable in the treatment of physical or biochemical brain injuries caused by trauma, infection, stroke, ischemia, and, particularly, malignant brain tumors, for which survival rates are notoriously poor.

The present invention also relates to a method of delivering a medicant to a malignant tumor in the brain or anywhere in the body of a mammalian subject. The method involves administering to the subject a potassium channel agonist, other than bradykinin or a bradykinin analog, under conditions and in an amount sufficient to increase the permeability to the medicant of a capillary or arteriole delivering blood to cells of the malignant tumor in the subject. Simultaneously or substantially simultaneously with the potassium channel agonist the medicant is administered to the subject, and it is delivered selectively to the malignant cells compared to non-malignant cells by virtue of the potassium channel agonist. The inventive method is useful in treating any kind of malignant tumor by increasing the selectivity of drug delivery to neoplastic tissue, thereby minimizing damage to non-malignant tissue from medicants, including cytotoxic chemotherapeutic agents, and focusing the therapeutic or diagnostic action of the agents. Thus, this invention, also directed to a method of treating a malignant tumor in a human subject, offers enhanced prospects of survival to cancer patients, with fewer harmful side effects.

The selectivity of the methods is based on the role of calcium- and ATP-dependent potassium transporters (channels) in mediating the permeability of microvasculature to various drugs, macromolecules, and viral particles, combined with the greater number of calcium- and ATP-dependent potassium channels present in abnormal brain vasculature or tumor neomicrovasculature compared to normal microvasculature.

The present invention also relates to a pharmaceutical composition that comprises a combination of a potassium channel agonist, other than bradykinin or a bradykinin analog, formulated in a pharmaceutically acceptable solution together with a medicant for delivery by intravascular infusion or bolus injection into a mammal, such as a human. The pharmaceutical composition is useful in practicing the inventive methods.

The invention also relates to a kit for enhancing the delivery of a medicant to an abnormal brain region and/or to a malignant tumor.

These and other advantages and features of the present invention will be described more fully in a detailed description of the preferred embodiments which follows.

BRIEF DESCRIPTION OF THE DRAWINGS

The file of this patent contains at least one drawing executed in color. Copies of this patent with color drawing (s) will be provided by the Patent and Trademark Office upon request and payment of the necessary fee.

DETAILED DESCRIPTION OF THE PREFERRED EMBODIMENTS

Figure 1A:
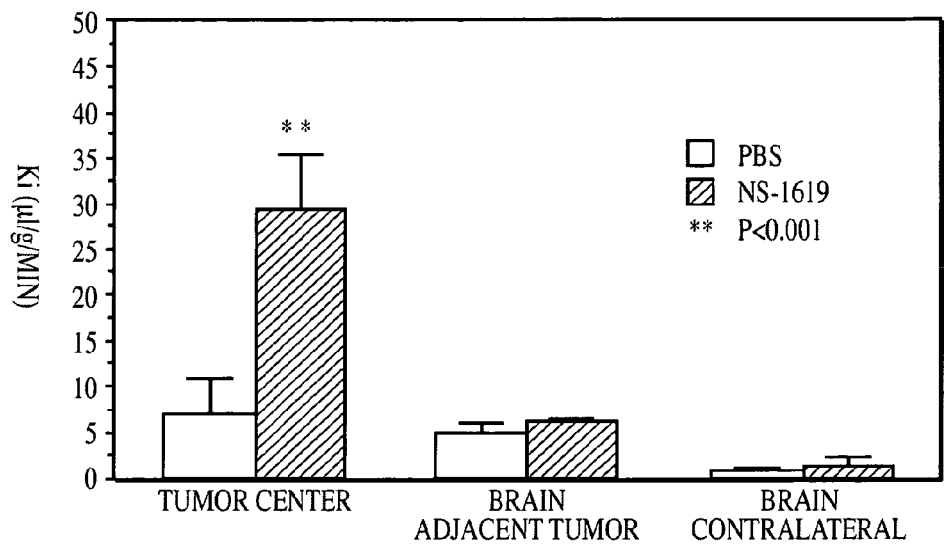
FIG. 1A shows the enhancing effect of NS-1619 on blood-tumor barrier permeability to [$^{14}$C]α-aminoisobutyric acid (AIB) tracer (left) compared to the effect on blood-brain barrier permeability in normal brain tissue adjacent (middle) and contralateral (right) to malignant RG2 glioma tissue in Wistar rats.

The inventive methods are useful for selectively delivering a medicant to abnormal brain regions and/or malignant tumors in mammalian subjects. The methods involve administering to the mammalian subject a potassium channel agonist, other than bradykinin or a bradykinin analog, under conditions and in an amount sufficient to increase the permeability to the medicant of a capillary or arteriole delivering blood to cells of the abnormal brain region and/or to malignant cells of a malignant tumor present in the subject. The increase in permeability ranges from at least 2-to 6-fold, compared to controls without the administration of a potassium channel agonist. The relative increase in permeability tends to be greater for large molecular weight medicants (e.g., about 10,000 to 250,000 D) than for smaller molecular weight substances (e.g., about 50–200 D).

The abnormal brain regions include regions of brain tissue physiologically directly affected by a physical or biochemical injury, for example, Alzheimer's disease, Parkinsonism, trauma, infection, stroke, brain ischemia, or regions of neoplastic growth within the brain, such as benign or malignant brain tumor tissues.

The present invention is also useful for selectively delivering a medicant to a malignant tumor in the brain or to a tumor elsewhere in the body of a mammalian subject. The inventive technology is useful in the treatment of all kinds of solid malignant tumors, including gliomas, glioblastomas, oligodendrogliomas, astrocytomas, ependymomas, primitive neuroectodermal tumors, atypical meningiomas, malignant meningiomas, neuroblastomas, sarcomas, melanomas, lymphomas, or carcinomas. The tumor to be treated can be contained in the skull, brain, spine, thorax, lung, peritoneum, prostate, ovary, uterus, breast, stomach, liver, bowel, colon, rectum, bone, lymphatic system, skin, or in any other organ or tissue of the subject.

The inventive methods are useful in treating any mammal, including a human, non-human primate, canine, feline, bovine, porcine or ovine mammal, as well as in a small mammal such as a mouse, rat, gerbil, hamster, or rabbit.

The potassium channel agonist is an activator of either a calcium-activated potassium channel ($K_{Ca}$) of any conductance level, whether of large, intermediate, or small conductance, or of an ATP-sensitive potassium channel ($K_{ATP}$). Examples of useful potassium channel agonists that are $K_{Ca}$ activators include 1,3-dihydro-1-[2-hydroxy-5-(trifluoromethyl)phenyl]-5-(trifluoromethyl)-2H-benzimidazol-2-one (NS-1619) or 1-ethyl-2-benzimidazolinone (1-EBIO). Other examples include soluble guanylyl cyclase activators, such as, metalloporphyrins (e.g., zinc or tin protoporphyrin IX), YC-1 (a benzyl indazole derivative), or guanylyl cyclase activating proteins (GCAPs).

Examples of useful potassium channel agonists that are $K_{ATP}$ activators include minoxidil (2,4-diamino-6-piperidino pyramidine-3-oxide; insoluble in water, soluble in ethanol 29 mg/mL), pinacidil ((+/−)-N-cyano-N'-4-pyridinyl-N"-(1, 2,2-trimethyl propyl)-guanidine; insoluble in water, soluble in ethanol 14 mg/mL]), (+)-cromakalim, (−)-cromakalim or levcromakalim, (+/−)-cromakalim, or diazoxide. Included among useful potassium channel agonists are pharmaceutically acceptable molecular conjugates or salt forms that still have activity as potassium channel agonists. An example is minoxidil sulfate, but other pharmaceutically acceptable salts comprise anions other than sulfate, such as carbonate, bicarbonate, nitrate, or the like. Other embodiments of pharmaceutically acceptable salts contain cations, such as sodium, potassium, magnesium, calcium, or the like. Other embodiments of useful potassium channel agonists are hydrochloride salts.

However, the potassium channel agonist employed in the inventive methods is one other than the vasodilator bradykinin (Arg-Pro-Pro-Gly-Phe-Ser-Pro-Phe-Arg)(SEQ ID NO: 1), or a polypeptide bradykinin analog, such as receptor mediated permeabilizer (RMP)-7 or A7 (e.g., Kozarich et al., U.S. Pat. No. 5,268,164 and PCT Application No. WO 92/18529). Other analogs of bradykinin include related peptide structures which exhibit the same properties as bradykinin but have modified amino acids or peptide extensions on either terminal end of the peptide. Examples of bradykinin analogs include [phe$^8$ (CH$_2$—NH) Arg$^9$-bradykinin, N-acetyl [phe$^8$ (CH$_2$—NH-Arg$^9$] bradykinin and desArg9-bradykinin.

In accordance with the inventive methods, the potassium channel agonist is administered by intravenous or intra-arterial injection or infusion. For treating an abnormal brain region, such as an intracranial tumor, the potassium channel agonist is preferably administered by intracarotid infusion. The amount of potassium channel agonist to be administered ranges from 0.075 to 1500 micrograms per kilogram body mass. For humans the range of 0.075 to 150 micrograms per kilogram body mass is most preferred. This can be administered in a bolus injection, but is preferably administered by infusion over a period of one to thirty minutes, and most preferably during a period of one to fifteen minutes. For example, in rats, a dose rate of about 0.75 to about 100 µg kg$^{-1}$ min$^{-1}$ is most suitable. At dose rates above about 100 µg kg$^{-1}$ min$^{-1}$ a concomitant fall in blood pressure has been observed In humans, effective dose rates are about 0.075 to about 15 µg kg$^{-1}$ min$^{-1}$, with cautious monitoring of blood pressure being advised. The practitioner skilled in the art is also cautious in regulating the total infusion volume, rate of liquid infusion, and electrolyte balance to avoid adverse physiological effects related to these.

Some potassium channel agonists, such as NS-1619, minoxidil, minoxidil sulfate, pinacidil, or diazoxide are not easily dissolved in water; in preparing these agents for administration, a suitable and pharmaceutically acceptable solvent, such as ethanol, can be used to dissolve the potassium channel agonist prior to further dilution with an infusion buffer. The skilled practitioner is cautious in regulating the final concentration of solvent in the infusion solution to avoid solvent-related toxicity. For example, a final ethanol concentration in an infusion solution up to 5–10% (v/v) is tolerated by most mammalian subjects with negligible toxicity.

While the inventive method does not depend on any particular mechanism by which increased microvascular permeability to the medicant is achieved, it is thought that administration of the potassium channel agonist increases potassium flux through potassium channels in endothelial cell membranes of the capillaries and arterioles delivering blood to abnormal brain regions and/or malignant tumors. This results in a loosening of tight junctions in the microvascular epithelium and/or increased pinocytotic activity, enhancing the uptake of medicants from the blood vessels. In practicing the inventive methods, it is not necessary to measure potassium channel activity (i.e., potassium cation flux therethrough). But the skilled artisan is aware that potassium flux can be measured by any suitable method, for example, by measuring cellular uptake of $^{42}$K$^+$ or $^{201}$Tl$^+$ or channel conductance using patch-clamp or microelectrode devices. (e.g., T. Brismar et al., *Thallium-201 uptake relates to membrane potential and potassium permeability in human glioma cells*, Brain Res. 500(1–2):30–36 [1989]; T. Brismar et al., *Mechanism of high K$^+$ and Tl$^+$ uptake in cultured human glioma cells*, Cell Mol. Neurobiol. 15(3): 351–60 [1995]; S. Cai et al., *Single-channel characterization of the pharmacological properties of the K(Ca2+) channel of intermediate conductance in bovine aortic endothelial cells*, J. Membr. Biol. 163(2):147–58 [1998]).

The medicant is administered simultaneously or substantially simultaneously with the potassium channel agonist, and the medicant is delivered by the blood stream selectively to the abnormal brain region and/or to the malignant cells compared to normal brain tissue or non-malignant cells. "Simultaneously" means that the medicant is administered contemporaneously or concurrently with the potassium channel agonist. "Substantially simultaneously" means that the medicant is administered within about one hour after the potassium channel agonist is last administered, preferably within about 30 minutes after, and most preferably, is administered simultaneously with the potassium channel agonist. Alternatively, "substantially simultaneously" means that the medicant is administered within about 30 minutes before, and preferably within about 15 minutes before the potassium channel agonist is first administered.

The methods of delivering a medicant to an abnormal brain region and/or to a malignant tumor in a mammalian subject are effective in selectively delivering any medicant across the microvascular of an abnormal brain region and/or malignant tumor. The medicant is a drug, i.e., a chemotherapeutic agent. Example of chemotherapeutic agents including therapeutic cytotoxic agents (e.g., cisplatin, carboplatin, methotrexate, 5-fluorouracil, amphotericin), "naked" DNA expression vectors, therapeutic proteins, therapeutic oligonucleotides or nucleotide analogs, interferons, cytokines, or cytokine agonists or antagonists, adrenergic agents, anticonvulsants, anti-trauma agents, or any neuropharmaceutical agent used to treat or prevent an injury or disorder of the brain. Chemotherapeutic agents also include ischemia-protective drugs such as N-methyl-D-aspartate (NMDA) receptor antagonists; antimicrobial agents, such as antibiotics; immunotoxins, immunosuppressants, boron compounds, monoclonal antibodies and specific antigen-binding antibody fragments (e.g., Fab, Fab', F(ab')$_2$, or F(v) fragments), and cytokines, such as interferons, interleukins (e.g., interleukin [IL]-2), tumor necrosis factor (TNF)-$\alpha$, or transforming growth factors (e.g., TGF-$\beta$).

The medicant also includes anticancer chemotherapeutic agents. Typically, anticancer chemotherapeutic agents are cytotoxic agents, such as 5-fluorouracil, cisplatin, carboplatin, methotrexate, daunorubicin, doxorubicin, vincristine, vinblastine, or a cytotoxic alkylating agent, such as, but not limited to, busulfan (1,4-butanediol dimethanesulphonate; Myleran, Glaxo Wellcome), chlorambucil, cyclophosphamide, melphalan, or ethyl ethanesulfonic acid. The anticancer chemotherapeutic agents are particularly useful in practicing the method of selectively delivering a medicant to a malignant tumor, in the brain or in any other tissue of the body, and in the method of treating a malignant tumor in a human subject.

Medicants also include any therapeutic viral particle, for example an adenovirus-derived or herpes simplex virus (HSV)-derived viral vector for delivering genetic material to a cellular target in vivo. Medicants also include diagnostic agents, such as imaging or contrast agents, for example, radioactively labeled substances (e.g., [$^{99}$Tc]-glucoheptonate), gallium-labeled imaging agents (e.g., gallium-EDTA), ferrous magnetic, fluorescent, luminescent, or iodinated contrast agents. Where suitable, any of the afore-mentioned medicants having anticancer activity can also be used in practicing the method of selectively delivering a medicant to a malignant tumor or the method of treating a malignant tumor in a human subject.

Thus, the medicant can be a molecular substance having a molecular weight between about 50 D and about 250 kD. Or it can be a particle, such as a viral particle, having a diameter between about 50 to 250 nanometers.

This is by no means intended to be an exhaustive list of the kinds of medicants that can be employed in practicing the inventive methods. The medicant can be, but is preferably not, an agent that is highly lipid soluble and thus inherently able to penetrate cell membranes, for example nitrosourea.

The amount of medicant that is employed is within a conventional dose range for each medicant, however by practicing the inventive method, the increased transvascular permeability afforded can provide a greater selective therapeutic effect per dose or permit a lower effective dose to be used, if desired, for example to lessen systemic toxic effects from anti-cancer medication in a particular subject.

The medicant is administered by any appropriate method that can deliver it to the blood stream. Typically, this is by intravenous, intramuscular, or intra-arterial (including intracarotid) injection or infusion. However, for some applications other acceptable delivery routes can be used as long as the dose of medicant enters the blood stream substantially simultaneously with the potassium channel agonist. Examples include ingestion (e.g., of a powder, suspension, solution, emulsion, tablet, capsule or caplet); subcutaneous injection; stereotactic injection; or transdermal or transmucosal delivery by adhesive patch, suppository or gel for delivery through the skin, mucosa or epithelium of the mouth including the sublingual epithelium, the rectum, or the vaginal epithelium.

Alternatively, the medicant is administered together with the potassium channel agonist in a pharmaceutical composition of the present invention. The inventive pharmaceutical composition comprises a combination of a potassium channel agonist, other than bradykinin or a bradykinin analog, as described above, formulated in a pharmaceutically acceptable solution together with a medicant, as described above, for delivery by intravascular infusion or bolus injection into a mammal, such as a human. The solution is thus suitably balanced, osmotically (e.g., about 0.15 M saline) and with respect to pH, typically between pH 7.2 and 7.5; preferably the solution further comprises a buffer, such as a phosphate buffer (e.g., in a phosphate buffered saline solution). The solution is formulated to deliver a dose rate of about 0.075 to 1500 micrograms of potassium channel agonist per kilogram body mass in a pharmaceutically acceptable fluid volume over a maximum of about thirty minutes. For human subjects, the solution is preferably formulated to deliver a dose rate of about 0.075 to 150 micrograms of potassium channel agonist per kilogram body mass in a pharmaceutically acceptable fluid volume over a period of up to about thirty minutes.

The invention also relates to a kit for enhancing the delivery of a medicant to an abnormal brain region and/or to a malignant tumor. The kit is an assemblage of materials or components, including a potassium channel agonist, other than bradykinin or a bradykinin analog, as described above. In addition, the kit contains instructions for using the potassium channel agonist to enhance the permeability of abnormal microvascular, including neomicrovasculature, to a medicant in general, or alternatively, to a particular medicant. Optionally, the kit also contains other components, such as a particular medicant in any pharmaceutically acceptable formulation, or paraphernalia for injection or infusion, for example syringes, infusion lines, clamps, and/or infusion bags/bottles, which can contain a pharmaceutically acceptable infusible formulation of the potassium channel agonist with or without a particular medicant also contained therein. The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures.

The foregoing descriptions of the methods and kits of the present invention are illustrative and by no means exhaustive. The invention will now be described in greater detail by reference to the following non-limiting examples.

EXAMPLES

Example 1

Methods

Malignant Cell Line and Tumor Implantation. A rat glioma cell line, RG2, was used for implantation of experimental brain tumors in Wistar rats. The techniques for RG2 cell propagation and maintenance in tissue culture have been described (Sugita, M. and Black, K. L., *Cyclic GMP-specific phosphodiesterase inhibition and intracarotid bradykinin infusion enhances permeability into brain tumors*, Cancer Res. 58(5):914–20 [1998]; Inamura et al. [1994]; Nakano, S. et al., *Increased brain tumor microvessel permeability after intracarotid bradykinin infusion is mediated by nitric oxide*, Cancer Res. 56(17):4027–31 [1996]). Briefly, RG2 cells derived from a rat glioma are kept frozen until use, then are thawed and maintained in a monolayer culture in F12 medium with 10% calf serum.

The Wistar rats (approximately 140–160 g body weight) were anesthetized with intra-peritoneal ketamine (50 mg/kg), and glial cells (1×10$^5$) were implanted into the right hemisphere, but not the contralateral hemisphere, by intracerebral injection suspended in 5 µL F12 medium (1–2% methylcellulose) by a Hamilton syringe. The implantation coordinates were 3-mm lateral to the bregma and 4.5 mm deep to the dural surface.

Intracarotid Infusion of Potassium Channel Activators. Seven days after implantation of RG2 cells, the rats were anesthetized as described above and prepared for permeability studies. Animals were infused with either NS-1619 (a selective large conductance Ca$^{2+}$-activated K$^+$ channel activator; RBI, Natick, Mass.) or minoxidil sulfate (a $K_{ATP}$ channel activator) into the right carotid artery at a dose rate of 7.5 µg kg$^{-1}$ min$^{-1}$ (in 53.3 µL/min) for 15 minutes, in an infusion vehicle of PBS, pH 7.4; 5% (v/v) ethanol. Ethanol (25% [v/v]) was used to dissolve the potassium channel agonists before dilution in PBS. For blood volume studies, 5 and 14 minutes after the start of the intracarotid infusion of potassium channel agonist compounds, [$^{14}$C] Dextran (100 µCi/kg; Dupont-New England Nuclear Co., Boston, Mass.) was injected as an intravenous bolus and maintained for 1 minute and 10 minutes to obtain two different time points. For regional permeability studies, 5 minutes after the start of the intracarotid infusion of vasoactive compounds, 100 µCi/kg of [$^{14}$C]α-aminoisobutyric acid (Dupont-New England Nuclear Co., Boston, Mass.) was injected as an intravenous bolus. A peristaltic withdrawal pump was used to withdraw femoral arterial blood at a constant rate of 0.083 mL/min immediately after the injection of the tracer to determine serum radioactivity. Fifteen minutes after the intracarotid infusion, rat decapitated and the brain rapidly removed and frozen for quantitative autoradiography.

Unidirectional Transport Constant ($K_i$). The unidirectional transfer constant $K_i$ for [$^{14}$C]α-aminoisobutyric acid was measured in normal tissue and tumor tissue as an indicator of permeability across the blood-tumor and blood-brain barriers. Quantitative autoradiography was used to obtain $K_i$ values (µL g$^{-1}$ min$^{-1}$). The initial rate for blood-to-brain transfer was calculated using a previously described equation. (Ohno, K, et al., *Lower limits of cerebrovascular permeability to nonelectrolytes in the conscious rat*, Am. J. Physiol. 235(3):H299–307, [1978]; Inamura, T., et al., *Bradykinin selectively opens blood-tumor barrier in experimental brain tumors*, J. Cereb. Flow Metab. 14(5):862–70 [1994]). Quantitative data were analyzed using, two group t-test and two-group Fisher's-exact test of equal proportions or equal means (equal numbers) at 90% power requires a minimum of 6 animals in each group to achieve statistical significance. Multiple treatment groups were compared with control group by ANOVA and P values determined by post-hoc Bonferroni test.

Dose-dependence studies. NS-1619 was dissolved in 25% ethanol and diluted with PBS to obtain various concentrations for infusion. NS-1619 was administered by intracarotid infusion (dose rates: 0, 13, 26.5, 53, 80, 100 and 110 µg kg$^{-1}$ min$^{-1}$; all at 53.3 µL/min) to RG2 glioma-bearing rats to determine a dose that produces increased permeability ($K_i$) of [$^{14}$C]-AIB, which was administered intravenously. $K_i$ determined as described above. Physiological parameters were monitored during the experiments.

Inhibition studies. Since NS-16129 increased permeability, the specificity of its effect was examined using the specific $K_{Ca}$ channel inhibitor, iberiotoxin (RBI, Natick, Mass.). Iberiotoxin (IBTX) was diluted in saline to a final concentration of 100 µg/mL. IBTX (2.3 µg kg$^{-1}$ min$^{-1}$) was co-infused with NS-1619 (26.5 µg kg$^{-1}$ min$^{-1}$) to block $K_{Ca}$ channel-induced permeability in abnormal capillaries in the RG2 glioma model. Seventeen rats were used for these studies (3 vehicle-only control [i.e., PBS±5% (v/v) ethanol]; 3 IBTX; 8 NS-1619; 3 NS-1619+IBTX). $K_i$ for [$^{14}$C]-AIB was determined by quantitative autoradiography as described earlier by Ohno et al. (1978).

Immunohistochemical analysis for $K_{Ca}$ channels. Brain sections (12 µm thick) obtained from the permeability studies were incubated with 1:100 dilution of affinity-purified $K_{Ca}$ channel antibody (Alomone Labs, Jerusalem, Israel) for 1 hour, and biotinylated horse anti-mouse immunoglobin (Vector Laboratories, Burlingame, Calif.) for 30 minutes. After washing 3 times with PBS, the peroxidase sites were visualized using an avidin:biotinylated enzyme complex (ABC) kit.

Example 2

Results

Potassium Channel Activators Selectively Increase Transport Across the Blood-tumor Barrier.

Figure 1B:
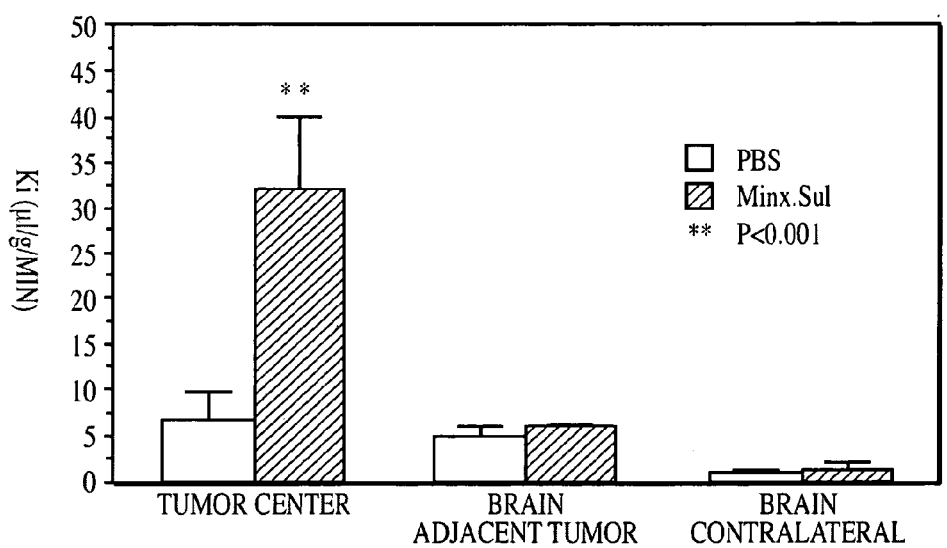
FIG. 1B shows the enhancing effect of minoxidil sulfate on blood-tumor barrier permeability to [$^{14}$C]AIB tracer (left) compared to the effect on blood-brain barrier permeability in normal brain tissue adjacent (middle) and contralateral (right) to malignant RG2 glioma tissue in Wistar rats.

When Wistar rats bearing implanted glioma cells were infused with either NS-1619 or minoxidil sulfate, at 7.5 µg kg$^{-1}$ min$^{-1}$ for 15 minutes, the unidirectional transport constant $K_i$ for [$^{14}$C]α-aminoisobutyric acid (AIB) was significantly increased by both NS-1619 and minoxidil sulfate with respect to transport across the neovasculature forming the blood-tumor barrier, but not with respect to transport across normal brain microvasculature. (FIGS. 1A and 1B). These results demonstrate that activation of potassium calcium channels selectively increases the permeability of molecules across the capillaries of solid malignant tumors compared to capillaries supplying normal brain tissue.

Figure 2:
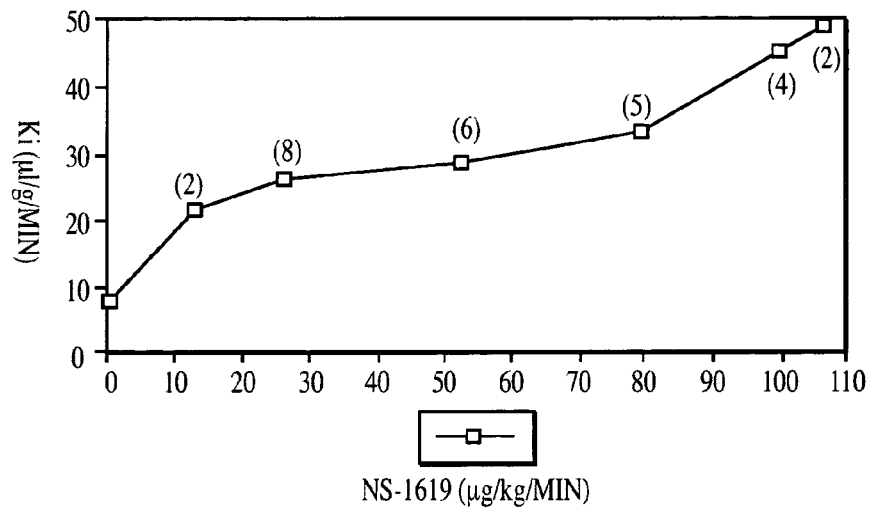
FIG. 2 shows a dose-response to NS-1619 in the unidirectional transfer constant $K_i$ for [$^{14}$C]α-aminoisobutyric acid in malignant RG2 glioma tissue in Wistar rats. $K_i$=μL/g/min.

The dose-dependent nature of this increased permeability is demonstrated in FIG. 2, which shows that increasing the dose of NS-1619 results in an increase in the unidirectional transfer constant $K_i$ for [$^{14}$C]α-aminoisobutyric acid in RG2 glioma capillaries. At higher doses (100 and 110 µg/kg/min) a significant drop in the arterial blood pressure of the rats was observed. The numbers of rats used in each group is shown in parentheses in FIG. 2.

Figure 3:
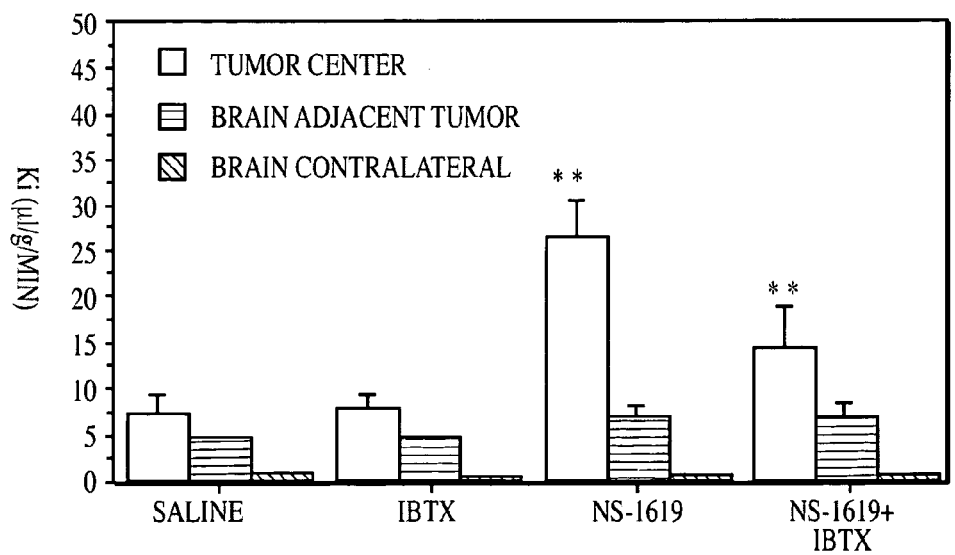
FIG. 3 shows specific inhibition by iberiotoxin (IBTX; 2.3 μg kg$^{-1}$ min$^{-1}$) of the permeability increasing effect of NS-1619 (26.5 μg kg$^{-1}$ min$^{-1}$). The $K_i$ was determined in RG2 tumor-bearing Wistar rats using [$^{14}$C]AIB with NS-1619 (26.5 μg kg$^{-1}$ min$^{-1}$) with or without IBTX (2.3 μg kg$^{-1}$ min$^{-1}$), for 15 minutes. The results are compared with PBS, pH 7.4 with or without 5% ethanol.

The specificity of this effect is demonstrated in FIG. 3, which shows that the ability of NS-1619 to increase the unidirectional transfer constant $K_i$ for [$^{14}$C]α-aminoisobutyric acid was inhibited by the $K_{Ca}$-channel-specific inhibitor iberiotoxin (IBTX). The $K_i$ was determined in RG2 tumor-bearing rats using [$^{14}$C] AIB with NS-1619 (26.5 μg min$^{-1}$ kg$^{-1}$) with or without IBTX (2.3 μg kg$^{-1}$ min$^{-1}$; n=3), for 15 minutes. Increase of $K_i$ in response to NS-1619 infusion (n=8;  P<0.001 compared with PBS with or without 5% ethanol) was attenuated by IBTX co-treatment. IBTX alone at the dose investigated did not affect the brain-tumor barrier permeability of abnormal capillaries. However, IBTX significantly (n=3,  P<0.001 compared with NS-1619-treated group) decreased NS-1619-induced increase of permeability ($K_i$), indicating a potassium channel-specific effect. Controls receiving PBS plus 5% ethanol were indistinguishable from controls receiving PBS minus ethanol.

Immunohistochemical Analysis Shows Potassium Channels Are More Abundant in Neovasculature and Malignant Cells Compared to Normal Tissue.

Figure 4A:
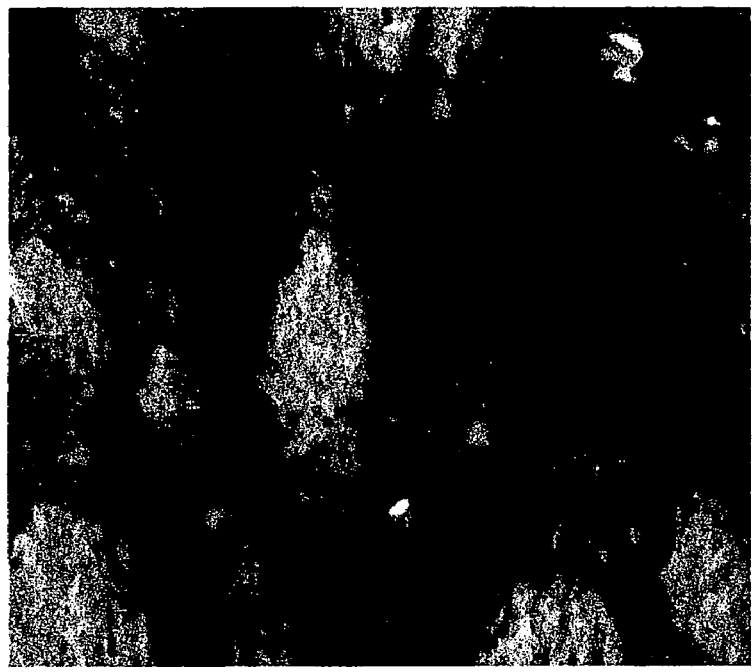
FIGS. 4A and 4B show intense over-expression of $K_{Ca}$ as indicated by anti-$K_{Ca}$ immunostain of glioma tissue (FIG. 4B), compared to normal contralateral brain tissue (FIG. 4A). Magnification is 100×.
Figure 4B:
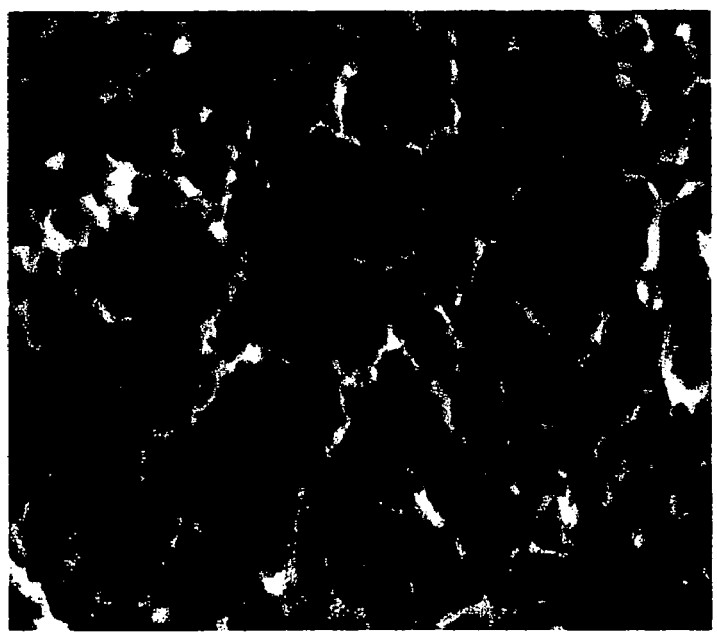

$K_{Ca}$ channel protein was immunolocalized using a specific antibody as described above. Immunohistochemical analysis showed that $K_{Ca}$ channels were selectively increased in tumor tissue and tumor capillaries in RG2 bearing rat brain sections, compared to sections of normal contralateral tissue. (FIG. 4). These immunohistochemical results are consistent with the permeability data in which activation of $K_{Ca}$ channel by NS-1619 selectively opened the blood-tumor barrier. (FIG. 1A).

Together, the permeability and immunohistochemical data demonstrate that compounds that activate potassium channels can be used to selectively increase delivery of anti-tumor compounds to malignant tumor tissue.

The foregoing examples being illustrative but not an exhaustive description of the embodiments of the present invention, the following claims are presented.

We claim:

1. A method of delivering a medicant to a brain tumor in a mammalian subject, comprising:
   administering to a mammalian subject having a brain tumor an agonist of an ATP-sensitive potassium channel, under conditions an in an amount sufficient to increase the permeability to the medicant of a capillary or arteriole delivering blood to cells of the brain tumor; and
   administering to the subject simultaneously or substantially simultaneously with the agonist the medicant, so that the medicant is delivered selectively to the cells of the brain tumor compared to normal brain regions.

2. The method of claim 1, wherein the potassium channel agonist is minoxidil.

3. The method of claim 1, wherein said mammal is a human.

4. The method of claim 1, wherein the medicant is a therapeutic cytotoxic agent.

5. The method of claim 1, wherein the agonist is administered by intravenous or intra-arterial infusion or injection.

6. The method of claim 1, wherein the agonist is administered by intracarotid infusion or injection.

7. The method of claim 1, wherein the agonist is administered to the mammalian subject by a bolus injection.

8. The method of claim 1, wherein the agonist is administered to the mammalian subject in an amount from about 0.075 to 1500 micrograms per kilogram body mass.

9. The method of claim 8, wherein the agonist is administered to the subject in an amount from about 0.075 to 150 micrograms per kilogram body mass.

10. The method of claim 1, wherein the agonist is administered to the mammalian subject at a dose rate of about 0.075 to about 100 μg kg$^{-1}$ min$^{-1}$ for up to about 30 minutes.

11. The method of claim 10, wherein the agonist is administered to the mammalian subject at a dose rate of about 0.075 to about 15 μg kg$^{-1}$ min$^{-1}$.

12. A method of selectively delivering a medicant to a brain tumor in a mammalian subject, comprising:
   administering to a mammalian subject having a brain tumor an agonist of an ATP-sensitive potassium channel, under conditions an in an amount sufficient to increase potassium flux through an ATP-sensitive potassium channel in an endothelial cell membrane of a capillary or arteriole delivering blood to cells of the brain tumor, whereby the capillary or arteriole is made more permeable to the medicant; and
   administering to the subject simultaneously or substantially simultaneously with the agonist the medicant so that the medicant is delivered selectively to the cells of the brain tumor compared to normal brain regions.

13. The method of claim 1, wherein the agonist is minoxidil sulfate.

14. The method of claim 1, wherein the agonist is diazoxide.

15. The method of claim 1, wherein the agonist is pinacidil.

16. The method of claim 1, wherein the agonist is cromakalim.

17. The method of claim 1, wherein the agonist is levcromakalim.

18. The method of claim 1, wherein the brain tumor is a benign tumor.

19. The method of claim 1, wherein the brain tumor is a malignant tumor.

20. The method of claim 1, wherein the brain tumor is a glioma, glioblastoma, oligodendroglioma, astrocytoma, ependymoma, primitive neuroectodermal tumor, atypical meningioma, malignant meningioma, or neuroblastoma.

21. The method of claim 1, wherein the medicant is administered via intravenous, intra-arterial, or intracarotid injection or infusion.

22. The method of any claim 1, wherein the agonist and the medicant are administered via intracarotid infusion or injection.

23. The method of claim 1, wherein the medicant is a protein.

24. The method of claim 1, wherein the medicant is a monoclonal antibody or antigen-binding antibody fragment.

25. The method of claim 1, wherein the medicant is a cytokine, cytokine antagonist, or cytokine agonist.

26. The method of claim 1, wherein the medicant is an interferon.

27. The method of claim 1, wherein the medicant is interleukin-2.

28. The method of claim 1, wherein the medicant is transforming growth factor beta.

29. The method of claim 1, wherein the medicant is a tumor necrosis factor alpha.

30. The method of claim 1, wherein the medicant is cisplatin or carboplatin.

31. The method of claim 1, wherein the medicant is methotrexate.

32. The method of claim 1, wherein the medicant is fluorouracil.

33. The method of claim 1, wherein the medicant is amphotericin.

34. The method of claim 1, wherein the medicant is daunorubicin.

35. The method of claim 1, wherein the medicant is doxorubicin.

36. The method of claim 1, wherein the medicant is vincristine.

37. The method of claim 1, wherein the medicant is vinblastine.

38. The method of claim 1, wherein the medicant is busulfan.

39. The method of claim 1, wherein the medicant is chlorambucil.

40. The method of claim 1, wherein the medicant is cyclophosphamide.

41. The method of claim 1, wherein the medicant is melphalan.

42. The method of claim 1, wherein the medicant is ethyl ethanesulfonic acid.

43. The method of claim 1, wherein the medicant is a diagnostic agent.

44. A method of delivering a medicant to a brain tumor in a mammalian subject, comprising:
administering simultaneously or substantially simultaneously to a mammalian subject having a brain tumor (i) minoxidil or minoxidil sulfate and (ii) a medicant, under conditions and in an amount sufficient to increase the permeability to the medicant of a capillary or arteriole delivering blood to cells of the brain tumor, so that the medicant is delivered selectively to the cells of the brain tumor compared to normal brain regions.

45. A method of delivering a therapeutic cytotoxic agent to an abnormal brain region in a mammalian subject, comprising:
administering simultaneously or substantially simultaneously to a mammalian subject having a brain tumor (i) minoxidil or minoxidil sulfate and (ii) a therapeutic cytotoxic agent, under conditions and in an amount sufficient to increase the permeability to the agent of a capillary or arteriole delivering blood to cells of the brain tumor, so that the agent is delivered selectively to the cells of the brain tumor compared to normal brain regions.

46. The method of claim 44, wherein the agent is cisplatin or carboplatin.

47. The method of claim 44, wherein the agent is methotrexate.

48. The method of claim 44, wherein the agent is 5-fluorouracil.

49. The method of claim 44, wherein the agent is amphotericin.

50. The method of claim 44, wherein the agent is daunorubicin.

51. The method of claim 44, wherein the agent is doxorubicin.

52. The method of claim 44, wherein the agent is vincristine or vinblastine.

53. The method of claim 44, wherein the agent is busulfan.

54. The method of claim 44, wherein the agent is chlorambucil.

55. The method of claim 44, wherein the agent is cyclophosphamide.

56. The method of claim 44, wherein the agent is melphalan.

57. The method of claim 44, wherein the agent is ethyl ethanesulfonic acid.

* * * * *

UNITED STATES PATENT AND TRADEMARK OFFICE
CERTIFICATE OF CORRECTION

PATENT NO. : 7,018,979 B1  Page 1 of 1
APPLICATION NO. : 09/491500
DATED : March 28, 2006
INVENTOR(S) : Keith L. Black et al.

It is certified that error appears in the above-identified patent and that said Letters Patent is hereby corrected as shown below:

Column 1, Line 4 under the title, please insert the following:

--GOVERNMENT LICENSE RIGHTS

The U.S. Government has a paid-up license in this invention and the right in limited circumstances to require the patent owner to license others on reasonable terms as provided for by the terms of Grant No. P01NX25554 awarded by the National Institutes of Health.--

Signed and Sealed this

Thirteenth Day of April, 2010

David J. Kappos
*Director of the United States Patent and Trademark Office*

UNITED STATES PATENT AND TRADEMARK OFFICE
CERTIFICATE OF CORRECTION

PATENT NO.        : 7,018,979 B1
APPLICATION NO.   : 09/491500
DATED             : March 28, 2006
INVENTOR(S)       : Keith L. Black et al.

It is certified that error appears in the above-identified patent and that said Letters Patent is hereby corrected as shown below:

In the Specification

Column 1, Line 4 under the title, please insert the following:

--GOVERNMENT LICENSE RIGHTS

The U.S. Government has a paid-up license in this invention and the right in limited circumstances to require the patent owner to license others on reasonable terms as provided for by the terms of Grant No. P0INS25554 awarded by the National Institutes of Health.--

This certificate supersedes the Certificate of Correction issued April 13, 2010.

Signed and Sealed this
First Day of October, 2013

Teresa Stanek Rea
*Deputy Director of the United States Patent and Trademark Office*

SEQUENCE LISTING

```
<160> NUMBER OF SEQ ID NOS: 1

<210> SEQ ID NO 1
<211> LENGTH: 9
<212> TYPE: PRT
<213> ORGANISM: Homo sapiens

<400> SEQUENCE: 1

Arg Pro Pro Gly Phe Ser Pro Phe Arg
 1               5
```